United States Patent [19]
Jung

[11] Patent Number: 5,759,487
[45] Date of Patent: Jun. 2, 1998

[54] METHOD AND APPARATUS FOR STERILIZING AND COLLECTING DUST IN AN AIR CONDITIONER

[75] Inventor: Choo Shick Jung, Suwon, Rep. of Korea

[73] Assignee: Samsung Electronics Co., Ltd., Suwon, Rep. of Korea

[21] Appl. No.: 535,960

[22] Filed: Sep. 28, 1995

[30] Foreign Application Priority Data

Jun. 13, 1995 [KR] Rep. of Korea ............... 1995-15556

[51] Int. Cl.$^6$ ............................................. A61L 2/00
[52] U.S. Cl. .................... 422/22; 422/5; 422/121; 422/186.07; 422/186.1; 422/186.15; 55/279
[58] Field of Search ....................... 422/121, 120, 422/108, 5, 22, 24, 186.15, 186.04, 186.07, 186.3, 186.1; 55/279

[56] References Cited

U.S. PATENT DOCUMENTS 5,334,347  8/1994  Hollander .................... 422/121

*Primary Examiner*—Hien Tran
*Attorney, Agent, or Firm*—Burns, Doane, Swecker & Mathis, L.L.P.

[57] ABSTRACT

The invention relates to an apparatus for sterilizing and collecting indoor pollutants and a method thereof, and more particularly to an apparatus and a method for sterilizing indoor floating funguses by use of a large quantity of ozone generated from a negative electrode discharge for an instant. The apparatus and method also improve dust collecting efficiency by controlling the use of positive and negative high voltage discharges based on a detected pollution level of the indoor air.

6 Claims, 10 Drawing Sheets

METHOD AND APPARATUS FOR STERILIZING AND COLLECTING DUST IN AN AIR CONDITIONER

BACKGROUND

This invention relates to an apparatus for sterilizing indoor floating funguses, which are harmful to the human body, for collection of indoor dust and a method thereof, and more particularly to the improvement of the apparatus for sterilizing indoor floating funguses in a short time and collecting dust by adjusting a high voltage discharge corresponding to a detected indoor pollution level and the method thereof.

Shown in FIG. 1, an air conditioner comprises an antifungal filter 3, a dust collecting filter 2, a deodorizing filter 2-1 inside a grille 1 for the purpose of collecting dust and deodorizing the indoor air. Generally an air conditioner has an evaporator 5 for cooling intaking air. When pollutants, such as dust, stick to the evaporator 5, the air flow cannot be smoothly maintained, and then the performance of the air conditioner deteriorates causing a pressure drop and impairing heat exchange. To prevent this deteriorating phenomena, the dust collecting filter 2 is disposed in front of an evaporator 5, inside a grille 1.

A ventilating cross fan 12 disposed at a bearing portion 10, 10-1, in a central part of an air conditioner, draws indoor air through inlets of a grille 1 and then the above-mentioned filters 2, 2-1, 3 filtrate the dust, smell, etc from the drawn air. The ventilating cross fan emits the cold air, heat-exchanged by an evaporator 5, through outlets in the grille 1. Blades 4-1, attached to a tray drain 4, are actuated by a stepping motor 4-3 which controls the direction and amount of airflow. The cross fan 12 is actuated by a fan motor 7, while the above-mentioned motors 4-3, 7 are controlled by a control portion 11.

The indoor air drawn through the inlets of the grille 1 passes through an antifungal filter 3 first, a dust collecting filter 2 and deodorizing filter 2-1 second and finally is emitted into the indoor atmosphere.

As an air clean key is inputted from a remote-controller (remocon, not shown) through a remocon receiver (not shown), a high voltage is given between an ionization line and a dust collecting board of an electric device for collecting dust (not shown). Therefore a corona discharge is generated between the ionization line and the dust collecting board. Pollutants floating in the drawn air are ionized by the corona discharge and collected on the dust collecting board. The usage of the dust collecting filter or board 2 and the electric device for collecting dust, prevents pollutants from collecting on the evaporator 5 and other elements. Consequently, clean air can be emitted into the indoor atmosphere.

But a problem exists in that the partial condensing water, remaining for a long time in an evaporator 5, creates moisture which propagates mold, bacteria, etc in the evaporator 5 as the condensing water, generated from the evaporator 5, flows into the condensing water bucket and is concurrently emitted outside through a drain tube. Some prior air conditioners have a sterilizing device and an antifungal device. The prior antifungal device, using cleansing water, has a problem in that a cleansing water container and a device pumping the cleansing water should be equipped therein. A prior sterilizing device using ozone has a problem in that ozone, harmful to the human body, is created in large amounts by a positive electrode discharge for long time.

A negative electrode discharge has better electrical characteristics and better dust collecting efficiency, but generates ozone, harmful to the human body, in quantity of ten times more than the positive electrode discharge. Therefore the prior apparatus, for collecting dust, has generally used a positive electrode discharge. But there are problems in that ozone, harmful to the human body, is created in large amounts in the case the positive electrode discharge, namely corona discharge, is performed for a long period of time and noise is generated by the friction of high voltage and pollutants piled on the dust collecting board.

SUMMARY

An object of the present invention is to provide an apparatus for sterilizing indoor floating funguses such as mold or bacteria, which are parasitic on elements of an air conditioner, and for collecting pollutants, like dust, of the indoor air drawn through the inlets.

Another object of the present invention is to provide an apparatus, for sterilizing and collecting dust, which can generate a large amount of ozone for a definite time period through use of a negative electrode discharge at a definite time on the occasion of non-operation of an air conditioner.

Another object of the present invention is to provide an apparatus, for sterilizing and collecting dust, which improves the dust collecting efficiency and minimizes the unhealthy ozone generation amount, by selecting a positive or a negative electrode discharge method as the high voltage discharge method in accordance with a detected indoor pollution level.

Another object of the present invention is to provide a method that sterilizes indoor floating funguses inside an air conditioner by generating large amounts of ozone for a specific time period using a negative electrode high voltage discharge, and efficiently collects pollutants with a minimum ozone generation amount by selecting a positive or a negative electrode discharge in accordance with the detected indoor pollution level.

According to an exemplary embodiment of the present invention, an apparatus for sterilizing and collecting dust comprises a high voltage generating portion having a rectangular wave generating circuit with the duty ratio capable of being adjusted, an inversion circuit inverting the rectangular wave into a pulsating current, a transformer, and a voltage multiplying circuit boosting the pulsating current to a high voltage, a pollution level sensor being exposed to the outside of an air conditioner for detecting the indoor air pollution level, a microcomputer which controls the high voltage generating portion, thereby bringing about a positive or negative electrode discharge, linked to the pollution level sensor, a power supply board, controlled by the microcomputer, for supplying electric power to the high voltage generating portion, a dust collecting board, linked to one output terminal of the high voltage generating portion and disposed in front of an evaporator, for collecting dust/etc and for generating ozone during a high voltage discharge, an ion generating portion linked through the power supply board to the other output terminal of the high voltage generating portion, and disposed within a definite interval from the dust collecting board, for ionizing atmospheric pollutants during a high voltage discharge and thereby causing the ionized pollutants to collect on the dust collecting board.

Additionally, according to an exemplary embodiment of the present invention, a method for sterilizing and collecting dust comprises a step to obtain a pollution level value through evaluation from the indoor pollution level data, detected by the pollution level sensor, a step for comparing the pollution level value with the predetermined pollution level reference value, a step for controlling the electric power supplied to the high voltage generating portion by use of the power supply board in accordance with the indoor air pollution level range, determined in the comparison step, and thereby collecting the indoor air pollutants ionized by the positive or negative electrode discharge of the high voltage generating portion on the dust collecting board, wherein each of the discharges are put into effect by control of the electric power, a step for determining whether or not the air conditioner is operating, a step for counting the time from the moment that the air conditioner is turned on, a step for determining whether the counted time is 24 hours, a step for stopping the counting, if the counted time is 24 hours, and for restarting the counting after the end of the sterilizing operation, a step for adjusting the microcomputer's output signal in case that the air conditioner is not operating and the counted time is at 24 hours, thereby causing the high voltage generating portion to institute the negative electrode discharge for a predetermined time interval in order that the indoor floating funguses are sterilized by a large quantity of ozone, generated by the discharge.

Accordingly, this invention brings about a clean indoor atmosphere by collecting dust during the air conditioner's operation, while sterilizing the indoor floating funguses during the conditioner's non-operation.

DETAILED DESCRIPTION OF THE PREFERRED EMBODIMENTS

Figure 1:
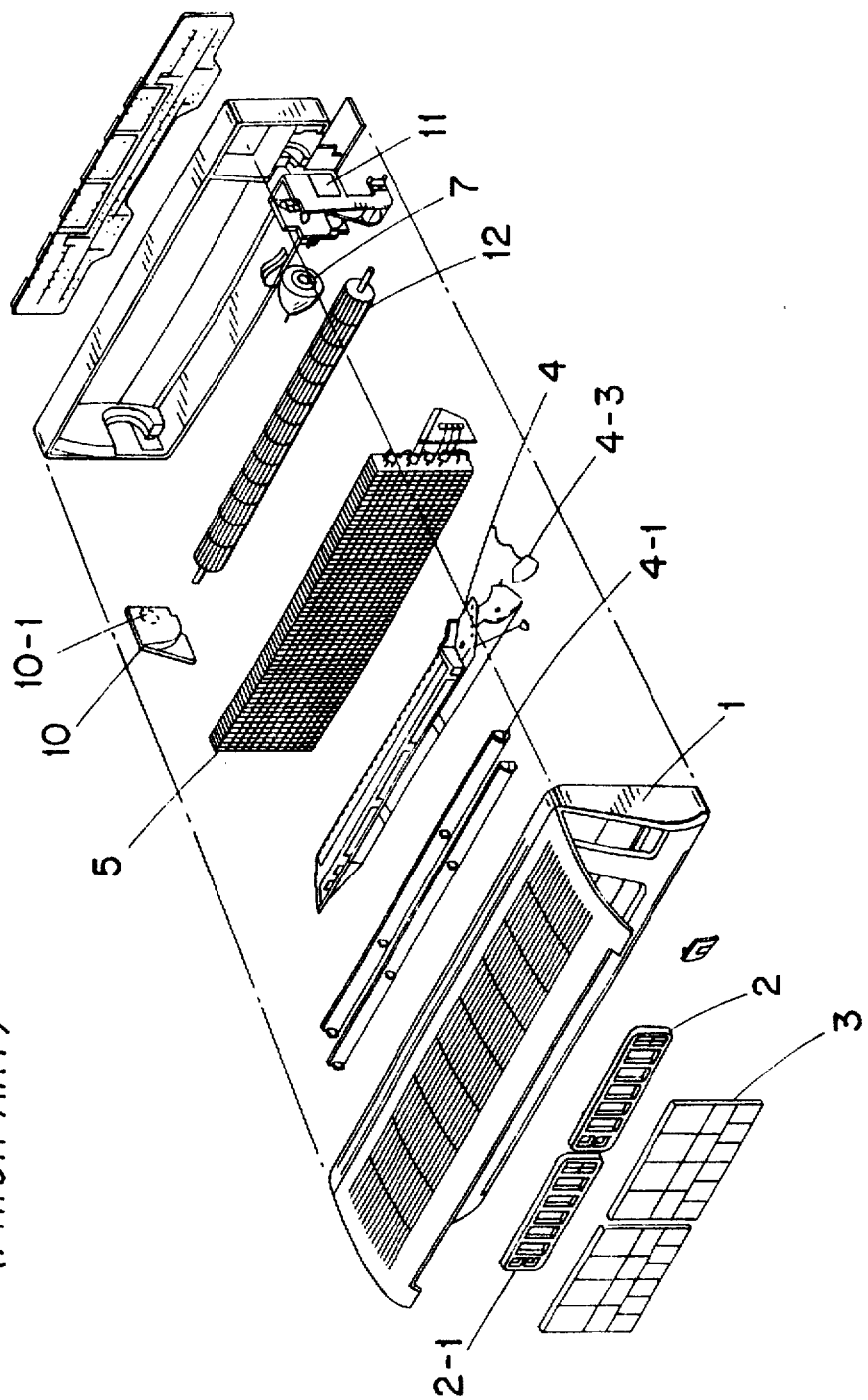
FIG. 1 is a perspective view of an air conditioner.
Figure 2:
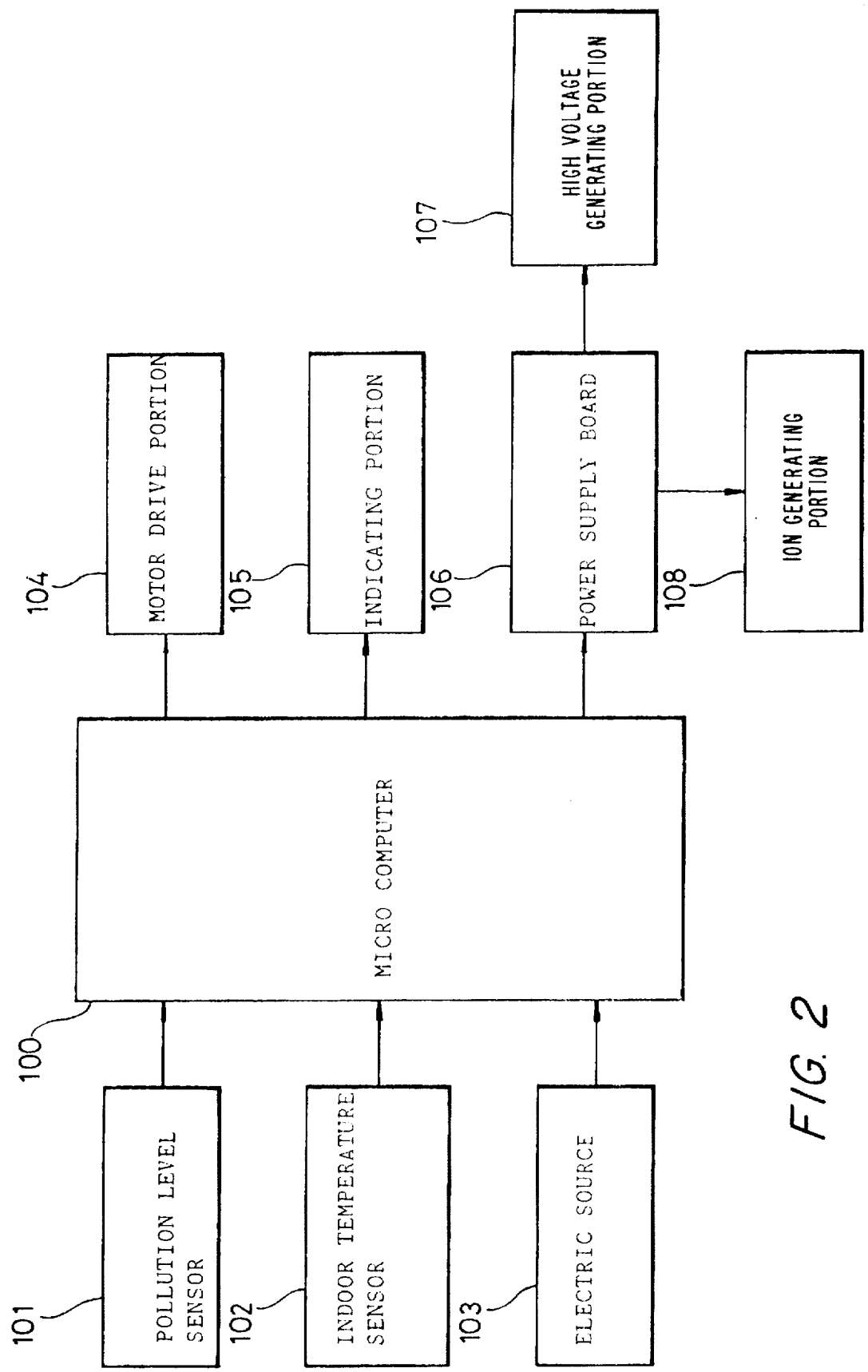
FIG. 2 is a block diagram of an air conditioner according to an exemplary embodiment of the invention.
Figure 7:
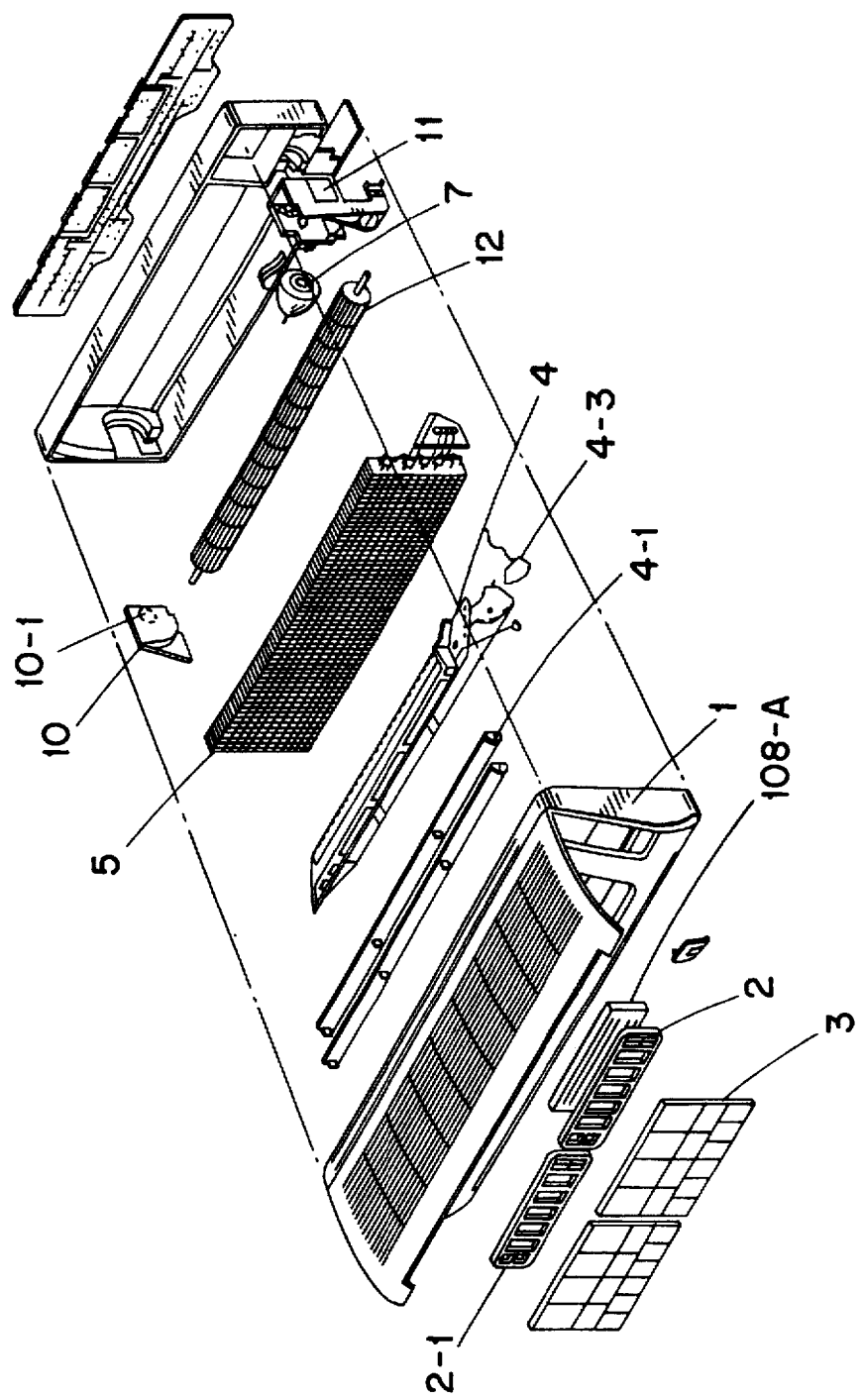
FIG. 7 is a view similar to FIG. 1 of an air conditioner according to the invention.

A block diagram of an air conditioner, comprising an apparatus for sterilizing and collecting dust, according to an exemplary embodiment of the invention is shown in FIG. 2. A pollution level sensor 101 and an indoor temperature sensor 102 are connected to a microcomputer 100, and are disposed on the outer surface of an air conditioner, and detect indoor air pollution level and indoor temperature, respectively. An electric source 103 is also connected to the microcomputer 100 for supplying electric power to every circuit. Detected data and electric power are transmitted from the pollution level sensor, the indoor temperature sensor and the electric source to the microcomputer. The microcomputer outputs signals to an indicating portion 105, displaying the operating condition of the air conditioner. To control the fan motor, used for ventilation, by using the inputted indoor temperature data, the microcomputer 100 outputs control signals to a motor drive portion 104 connected to the fan motor. Additionally, in order to collect the pollutants on the dust collecting board of the apparatus by using the indoor air pollution level data inputted from the pollution level sensor 101, the microcomputer 100 outputs control signals to a power supply board 106 which causes the high voltage generating portion 107 to discharge. According to the microcomputer's control, the power supply board 106 supplies electric power to the high voltage generating portion 107 so that a positive or negative electrode discharge from the high voltage generating portion 107 occurs. The ionization lines of the ion generating portion 108 are connected to the power supply board 106 and disposed in close vicinity to the dust collecting board. Through the power supply board 106, the ionization lines 108A of the ion generating portion 108 (FIG. 7) are connected to one output terminal of the high voltage generating portion 107. Thus the ionization lines of an ion generating portion 108 and one output terminal of the high voltage generating portion 107 are formed as common electrodes with the same polarity. Accordingly, the ionization lines generate positive or negative ions by use of a positive or negative electrode discharge occuring in accordance with the voltage polarity of one output terminal in the high voltage generating portion 107. Additionally, the other output terminal, of the high voltage generating portion 107, is connected with the dust collecting board or filter 2. The high voltage generating portion 107 and the ion generating portion 108 produce a predetermined high voltage onto the ionization lines and the dust collecting board. Thereby, a corona discharge, occurring between the ionization lines and the dust collecting board, causes the pollutants of the ambient indoor air to be collected on the dust collecting board.

Figure 3:
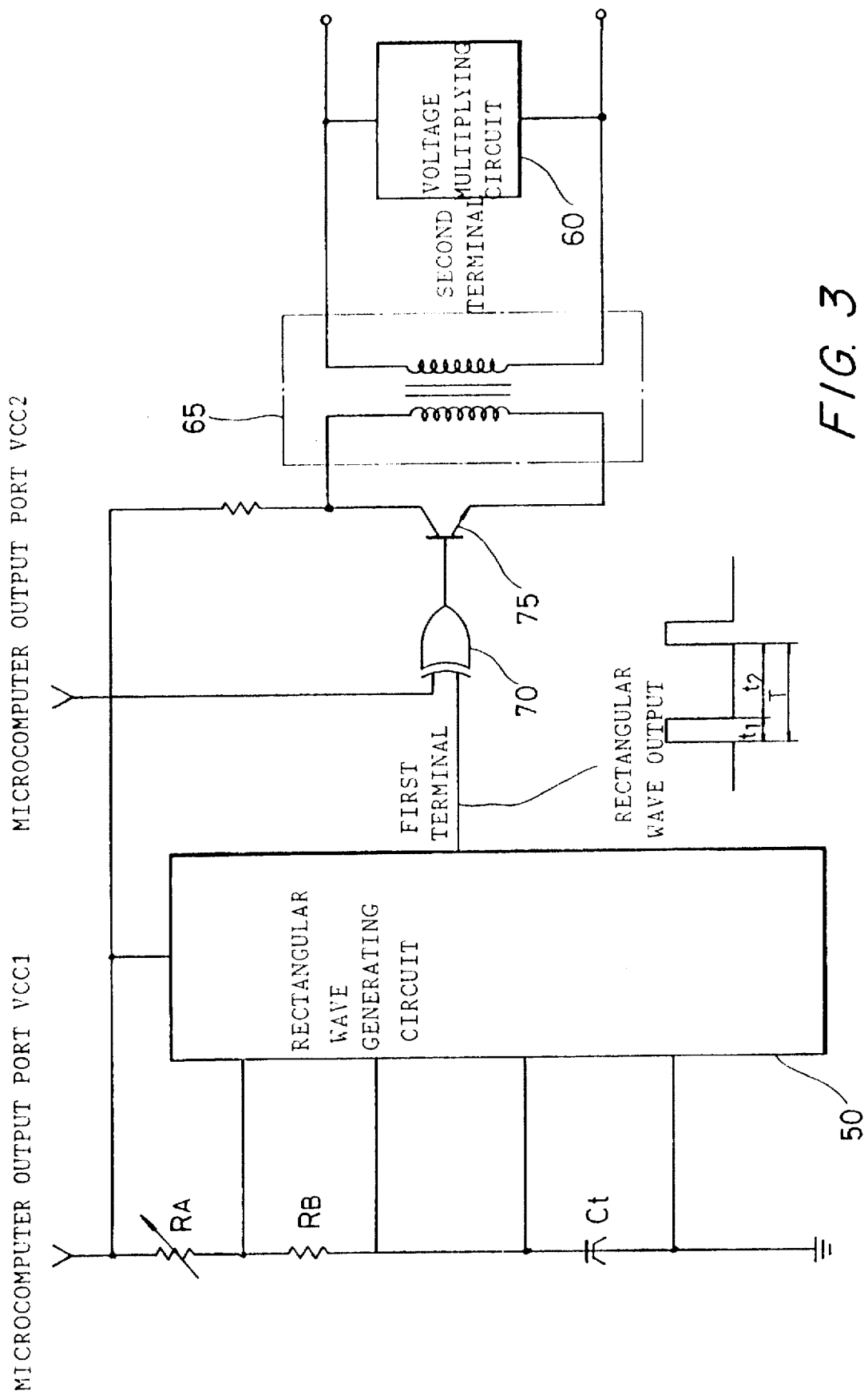
FIG. 3 is a circuit diagram of a high voltage generating portion according to an exemplary embodiment of the invention, FIGS. 4(a), (b) are output diagrams of the first terminal of the high voltage generating portion according to an exemplary embodiment of the invention, FIGS. 5(a), (b) are output diagrams of the second terminal of the high voltage generating portion according to an exemplary embodiment of the invention, FIGS. 6(a), (b) are a flow chart of a method for sterilizing and collecting dust according to an exemplary embodiment of the invention.

FIG. 3 is a circuit diagram of a high voltage generating portion 107 shown in FIG. 2. A rheostat $R_A$, a resistor $R_B$ and a capacitor Ct are disposed between a rectangular wave generating circuit 50 and an output port VCC1 of the microcomputer which supplies the rectangular wave generating circuit 50 with electric power outputted from the power supply board in accordance with the control signal of the microcomputer. A high level time interval $t_1$ and a low level time interval $t_2$, of the cycle of rectangular wave outputted from the rectangular wave generating circuit 50, are determined by the following formulas (1):

$$t_1 = 0.693(R_A + R_B) \cdot Ct$$
$$t_2 = 0.693 R_B \cdot Ct \qquad (1)$$

The time period T and the frequency f of the rectangular wave are determined by the following formulas (2):

$$T = t_1 + t_2 = 0.693(R_A + 2R_B) \cdot Ct$$

$f=1/T=1.44/((R_A+2R_B) Ct)$       (2)

Accordingly, the duty ratio is determined by the resistors ($R_A$, $R_B$) and the capacitor Ct. The output of the voltage multiplying circuit 60 described below changes on the basis of the duty ratio. Namely, the higher the duty ratio, the higher the output of the voltage multiplying circuit 60.

The exclusive-OR circuit portion 70 has two inputs, which are respectively connected to the output terminal of the rectangular wave generating circuit 50 and the output port VCC2 of the microcomputer which supplies the rectangular wave generating circuit 50 with an electric signal outputted from the power supply board in accordance with the control signal of the microcomputer. If the output port VCC2 is electrically off, the output of the exclusive-OR circuit portion 70 is same as that of the output of the rectangular wave generating circuit 50. On the other hand, as the output port VCC2 is electrically on, the output of the rectangular wave generating circuit 50 is reversed by passing through the exclusive-OR circuit portion 70. Thus, when the output of the rectangular wave generating circuit 50 is low or high, the exclusive-OR circuit portion 70 outputs high or low. The output of the exclusive-OR circuit portion 70 is connected to the base of a npn (negative-positive-negative) transistor 75.

The emitter of the npn transistor 75 is connected to one terminal of the transformer 65. In addition, the collector, of the npn transistor 75, is connected to the microcomputer output port VCC1 through the rectangular wave generating circuit 50 and to the other terminal of the transformer 65. The transistor 75 inverts the rectangular wave output, of the exclusive-OR circuit portion 70, to a pulsating wave and then outputs it to a transformer 65 disposed in the front of the voltage multiplying circuit 60. The output voltage of the transistor 75 is raised up by the transformer 65 and is then re-increased to several KV through the voltage multiplying circuit 60. The multiplied voltage is discharged to the dust collecting board (not shown) disposed in the front of the evaporator.

The reason for adding the voltage multiplying circuit 60 to the transformer 65 is that the capacity of the transformer 65 should be large as possible in order to obtain the high voltage necessary for a discharge. That is, the size of an air conditioner should be larger in proportion to its capacity. Therefore, it is necessary for a small-sized air conditioner to raise the output voltage of the transistor 75 up to its maximum by a small-size, small-capacity transformer 65 and then up to several KV enough for the corona discharge by the voltage multiplying circuit 60.

One output terminal of the high voltage generating portion is connected to the ionization line of the ion generating portion 108 shown in FIG. 2 through the power supply board 106. The other output terminal of the high voltage generating portion is connected to the dust collecting board (not shown). Therefore, in the case of a positive electrode discharge, the ionization line becomes a positive electrode and the dust collecting board a negative electrode. As a result of the positive electrode discharge, an electric field forms between the ionization line and the dust collecting board. Dust particles are electrified as positive charges by an electric field and collected onto the negative electrode dust collecting board.

On the other hand, a negative electrode discharge is accomplished by the ionization line being charged as a negative electrode and the dust collecting board as a positive electrode. Dust particles are electrically charged into negative ions by the ionization lines as negative electrodes and then collected onto the positive electrode dust collecting board.

In short, the rectangular wave is generated at the point of the first terminal shown in FIG. 3 and influences the voltage multiplying circuit 60. The voltage multiplying circuit 60 outputs the high voltage in accordance with the signals of the output ports VCC1, VCC2 of the microcomputer in order that a positive or negative electrode discharge may occur. Namely, if VCC1 is on and VCC2 is off, a negative electrode discharge occurs. Reversely, as VCC1 is off and VCC2 is on, a positive electrode discharge occurs.

Figure 4A:
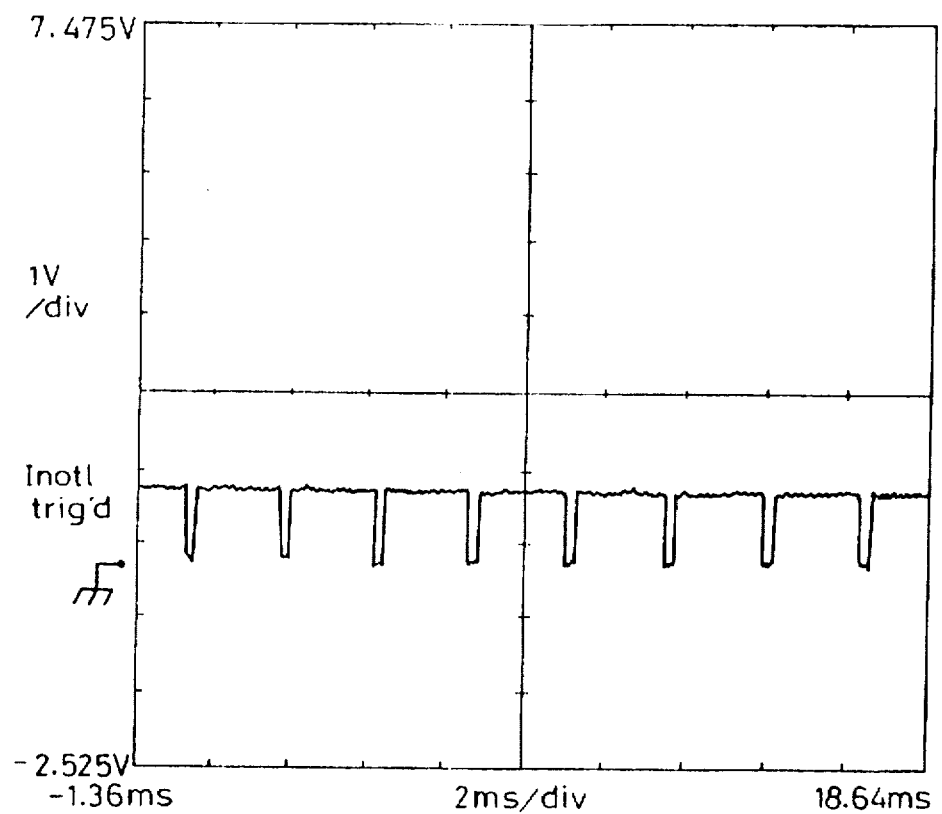
Figure 4B:
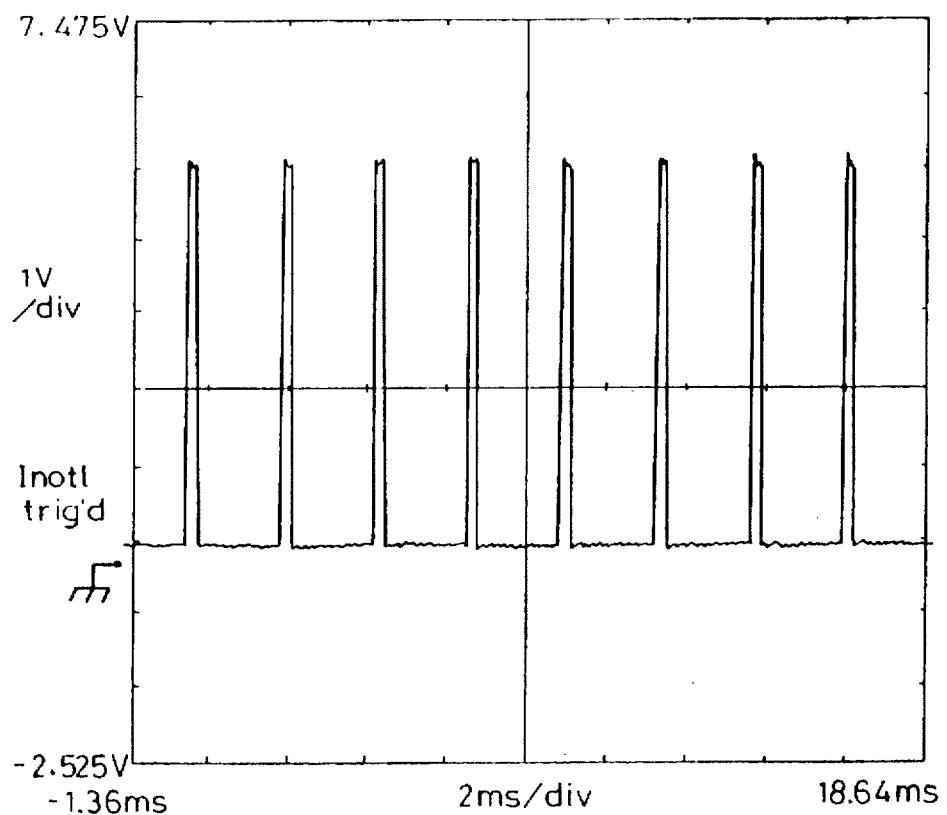
Figure 5A:
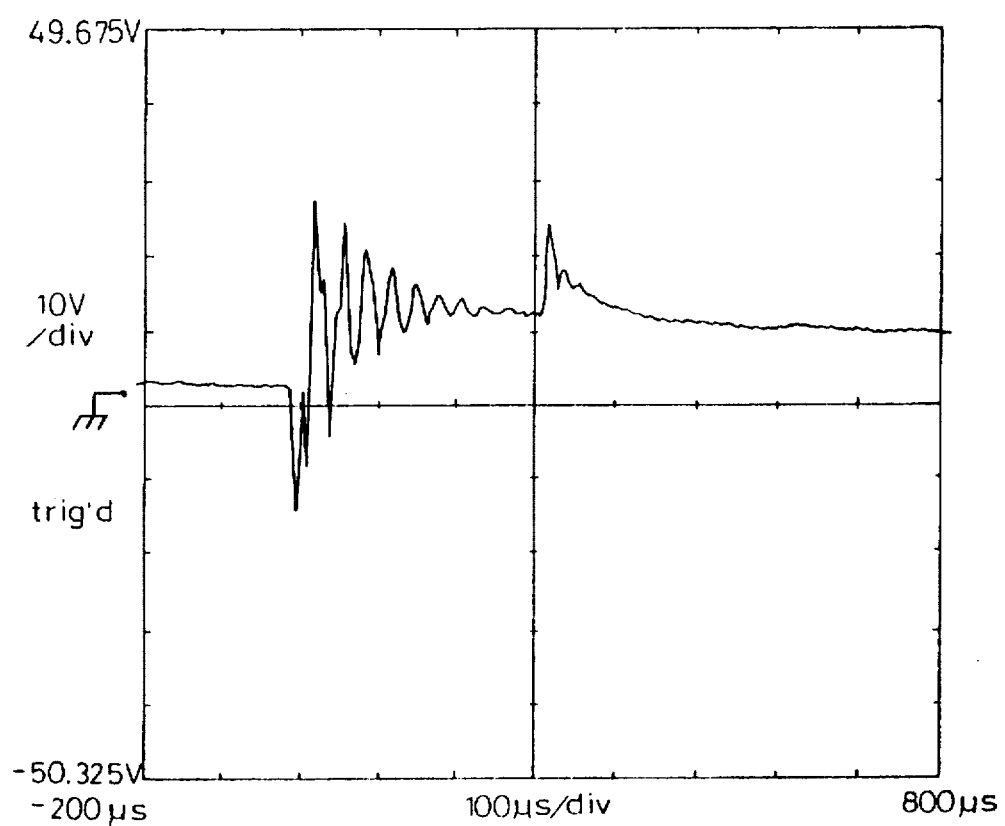
Figure 5B:
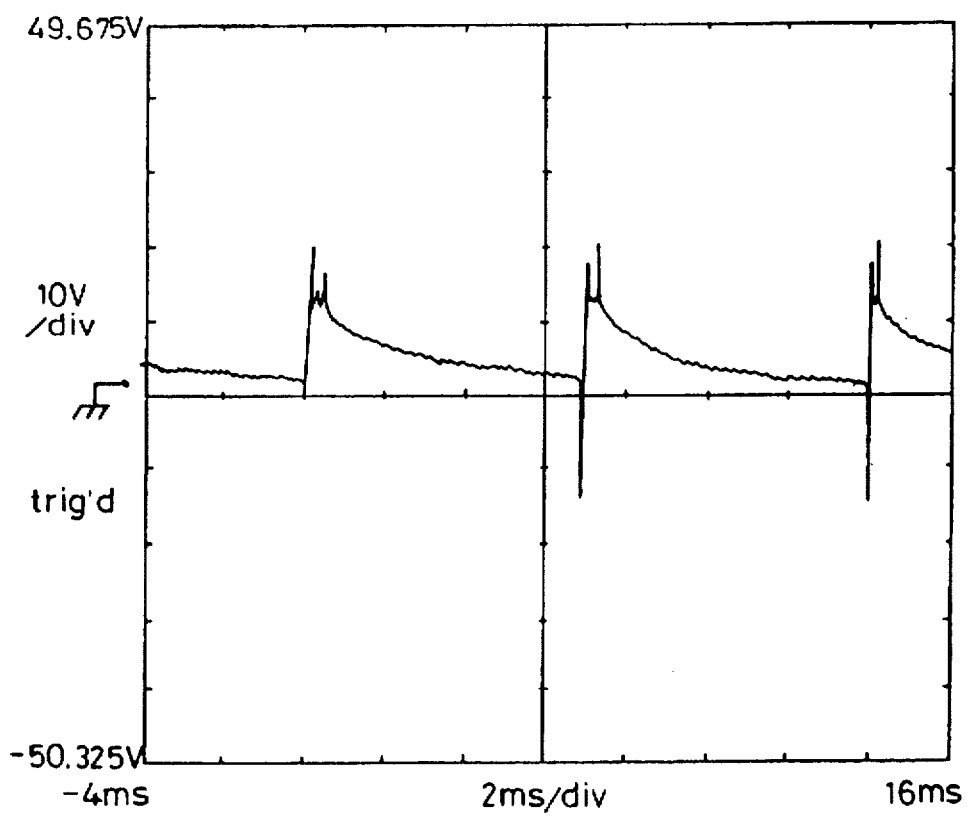

FIGS. 4(a), (b) illustrate the rectangular voltage waves at the first terminal. That is, FIG. 4(a) shows the voltage wave having the duty ratio, 90.13%, FIG. 4(b) is a drawing illustrating the voltage wave for which the duty ratio is 10.13%. FIGS. 5(a), (b) illustrate the output voltage waves at the point of the second terminal shown in FIG. 3, where FIG. 5(a) shows the second terminal voltage wave corresponding to the rectangular wave with the duty ratio, 90.13% of FIG. 4(a), while FIG. 5(b) is the drawing of the second terminal voltage wave corresponding to the rectangular wave with the duty ratio, 10.13% of FIG. 4(b).

A positive electrode discharge or the negative electrode discharge is generated at the output end of the voltage multiplying circuit 60 by control of the output ports, VCC1, VCC2 of the microcomputer in accordance with the indoor air pollution level, and consequently the indoor air pollutants are efficiently collected onto the dust collecting board. In addition, indoor floating funguses in the air conditioner can be sterilized by large quantities of ozone generated from the negative electrode discharge in a moment.

Figure 6A:
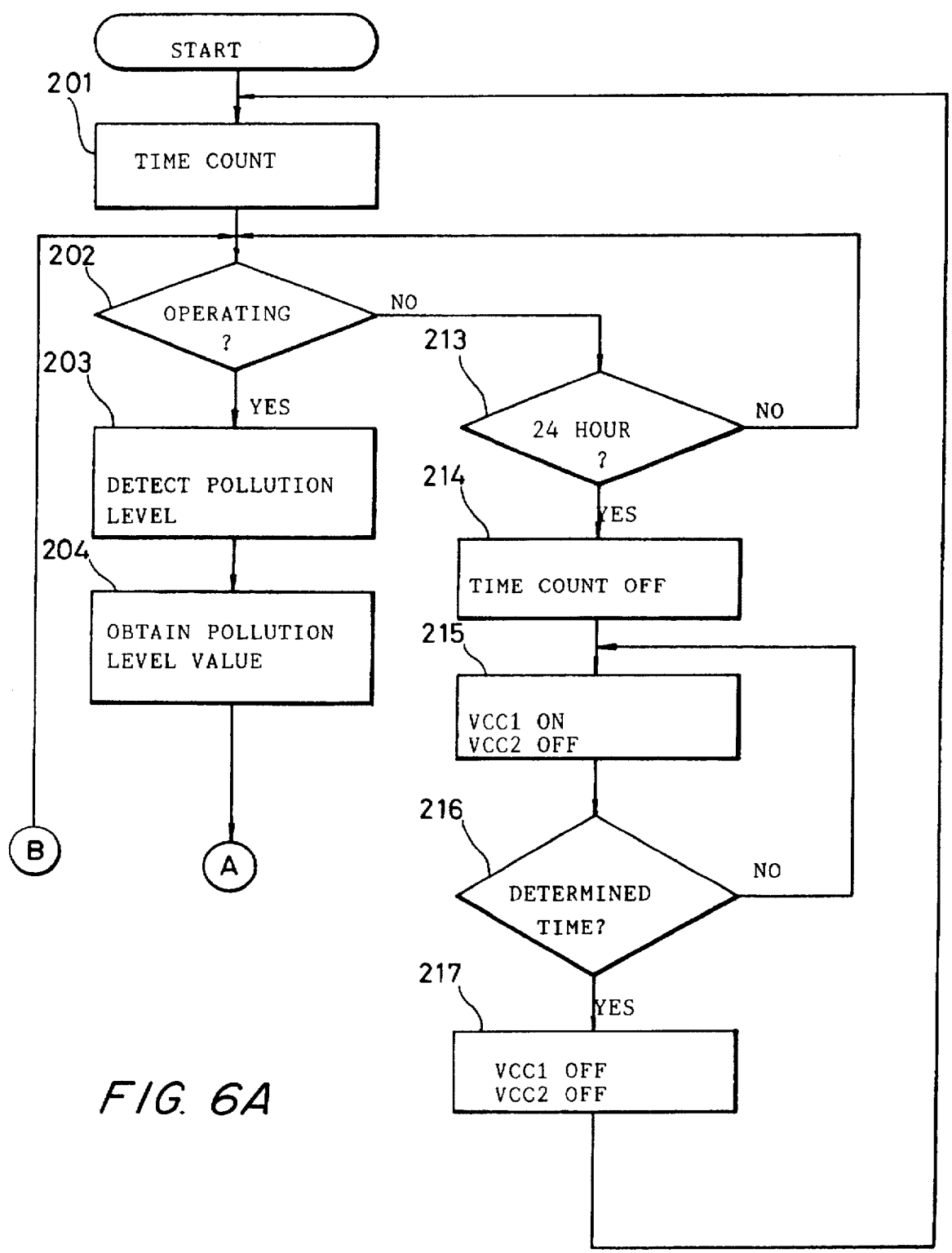
Figure 6B:
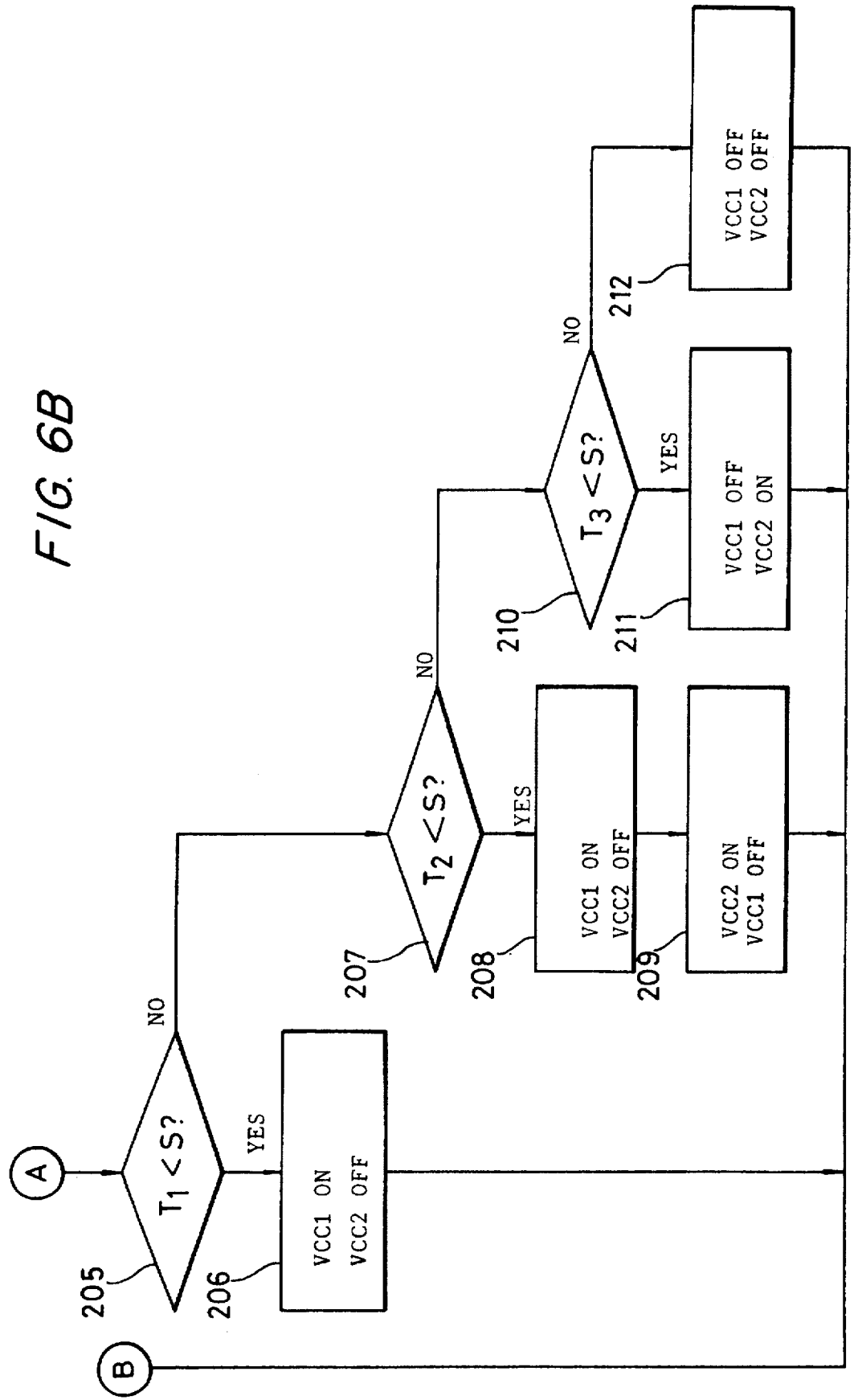

FIGS. 6(a), (b) show the method for sterilizing and collecting dust accomplished by the microcomputer, used in the apparatus for sterilizing and collecting dust according to an exemplary embodiment of the invention. As soon as the air conditioner is turned on, it begins to count time (step 201). It is then determined whether the air conditioner is operating under the state that time is counted up (step 202). If the air conditioner is operating, the pollution level is detected by the indoor air pollution level sensor (step 203) and then the pollution level value S is evaluated on the basis of the signal outputted from the sensor (step 204).

The detected pollution level value S is successively compared with the data $T_1$, $T_2$, $T_3$ which are the predetermined pollution level values as the references satisfying $T_1>T_2>T_3$ in magnitude. According to the pollution level range determined by the comparisons, the microcomputer controls the output ports so that the appropriate corona discharge is generated at the output end of the high voltage generating portion. If the pollution level value S is greater than the predetermined value $T_1$, in comparison of S with $T_1$ (step 205), the microcomputer activates the output port VCC1 to ON and deactivates VCC2 to OFF (step 206). As a result of the change, a negative electrode discharge is generated for a desired time interval (ex. two minutes) at the output end of the high voltage generating portion so that a large quantity of pollutant can be collected. A negative electrode discharge has a better dust collecting efficiency than a positive electrode discharge.

In case of $T_2<S<T_1$ (step 207), the microcomputer maintains VCC1 to ON and VCC2 to OFF so as to generate a negative electrode discharge for a one minute interval (step 208), and next reverses VCC2 to ON and VCC1 to OFF so that the positive electrode discharge is generated for a one minute interval (209). In the case where the pollution level value S is in the range of $T_3$ to $T_2$ (step 210), the microcomputer turns VCC1 off and VCC2 on so as to generate a positive electrode discharge for a desired time interval (step 211).

If the detected pollution level value S is less than the predetermined pollution level value $T_3$, the microcomputer deactivates VCC1, VCC2 to OFF and as a consequence the corona discharge is not generated (step 212).

Additionally, if the air conditioner is not in operation (step 202) and the counted time is 24 hours (step 213), the microcomputer stops counting time (step 214), and turns VCC1 on and VCC2 off for a desired time interval (step 215). As a consequence, a large quantity of ozone is generated by the negative electrode discharge, sterilizing in an instant the indoor floating funguses, being parasitic on the condensing water bucket and the condenser. After a desired time, the microcomputer deactivates the output ports VCC1 and VCC2 to stop the high voltage discharge (steps 216 and 217). The microcomputer restarts the time count and then makes the negative electrode discharge generated every 24 hours under the condition that the air conditioner is not in operation.

In FIG. 3, the rectangular wave generating circuit 50 may consist of flip-flops, and the exclusive-OR circuit 70 may consist of transistors and buffers.

In addition, it is possible to change the efficiency of the sterilization and dust collection by controlling the duty ratio of the rectangular wave.

In prior art, there is a deficiency in that ozone harmful to the human body exists for long period of time because the indoor floating funguses, being parasitic on the condensing water bucket and the condenser, are sterilized, while the indoor air pollutants are collected by the long time positive electrode discharge. In addition, in prior art, the short time positive electrode discharge deteriorates the dust collecting efficiency and the sterilizing power.

However, according to this invention, an apparatus for sterilizing and collecting dust and a method thereof has the effect that the instant negative electrode discharge generates a large quantity of ozone which sterilizes every determined time, while the dust collecting efficiency and the sterilizing power are raised for an instant by using a suitable high voltage discharge by the determination of the high voltage discharge method whether a positive electrode discharge or a negative electrode discharge, based on the detected indoor pollution level. That is to say, the sterilizing effect is accomplished every determined time by a negative electrode discharge which generates a large quantity of ozone for an instant. In addition, there is the dust collecting effect in the case where a large quantity of pollutant is collected for an instant by a negative electrode discharge, which has a better dust collecting efficiency than a positive electrode discharge when the indoor pollution level is high, and pollutant is collected by a positive electrode discharge generating a small quantity of ozone harmful to human body in case of the low indoor pollution level.

What is claimed is:

1. An air conditioner, comprising:

a housing forming an air inlet and an air outlet;

a blower for circulating indoor air along an air travel path from the inlet to the outlet;

an evaporator arranged in the air travel path for exchanging heat with the indoor air;

a pollution level sensor arranged to be exposed to indoor air for detecting an air pollution level of the indoor air;

a voltage generator for selectively generating negative and positive voltage discharges, the voltage generator comprising a rectangular wave generator having an adjustable duty ratio, the voltage generator including first and second output terminals, an ion generator operably connected to the second output terminal for being energized selectively thereby to positive and negative polarities and for charging pollutants in the air travel path to the corresponding polarity;

a dust collecting board disposed upstream of the evaporator and operably connected to the first output terminal for being charged to a polarity opposite a polarity to which pollutants are charged by the ion generator, for collecting the changed pollutants; and a microprocessor operably connected to the voltage generator for charging both of the ion generator and dust collecting board to collect indoor air pollutants during operation of the evaporator based on the detected air pollution level, and for charging only the ion generator at a negative polarity to generate ozone to sterilize during non-operation of the evaporator.

2. The apparatus of claim 1, wherein the voltage generator further comprises:

an exclusive-OR circuit having a first input connected to an output terminal of the rectangular wave generator and a second input connected to a second output port of the microprocessor;

an inversion circuit which inverts a rectangular received from an output of the exclusive-OR circuit into a pulsating current;

a transformer connected to the inversion circuit;

a voltage multiplying circuit, connected to a secondary terminal of the transformer, for boosting a voltage received from the transformer and for generating the negative and positive voltage discharges; and wherein the negative and positive voltage discharges are controlled with the first and second output ports of the microprocessor.

3. The apparatus of claim 2, wherein the rectangular wave generator further comprises a rheostat, a resistor, and a capacitor for adjusting the duty ratio of the rectangular wave generator, thereby controlling a dust collecting efficiency and a sterilizing efficiency of the apparatus.

4. The apparatus of claim 2, wherein the inversion circuit comprises a transistor having a base connected to the output of the exclusive-OR circuit, a collector connected to the first output port of the microprocessor and to a primary terminal of the transformer, and an emitter connected to the primary terminal of the transformer.

5. A method for sterilizing and collecting dust in an air conditioner, comprising the steps of:

obtaining a pollution level value of indoor air with a pollution level sensor;

comparing the pollution level value with a predetermined pollution level reference value;

controlling electric power supplied to a voltage generator based on the comparison between the pollution level value and the predetermined pollution level reference value, to thereby collect indoor air pollutants ionized by at least one of a positive electrode discharge and a negative electrode discharge generated by the voltage generator;

determining whether the air conditioner is operating;

counting a time from a point at which the air conditioner is turned on;

determining whether the counted time is 24 hours;

stopping the counting of time if the counted time is 24 hours, and restarting the counting of time after a sterilization operation; and directing the voltage generator to generate the negative electrode discharge for a predetermined time period to sterilize indoor floating funguses by ozone generated from the negative electrode discharge when the air conditioner is not operating and the counted time is 24 hours.

6. An air conditioner, comprising:

a housing forming an air inlet and an air outlet;

a blower for circulating indoor air along an air travel path from the inlet to the outlet;

an evaporator arranged in the air travel path for exchanging heat with the indoor air;

a pollution level sensor arranged to be exposed to indoor air for sensing an air pollution level of the indoor air;

a microprocessor, which receives a signal from the pollution level sensor, for controlling a cleaning operation of the air conditioner by use of at least one of a negative voltage discharge and a positive voltage discharge;

a voltage generator for generating the negative and positive voltage discharges based on a signal received from the microprocessor, the voltage generator including a rectangular wave generator having an adjustable duty cycle, wherein adjustment of the duty cycle controls a voltage level output from the voltage generator, and wherein the voltage generator is controlled by the microprocessor to generate at least one of the negative voltage discharge and the positive voltage discharge based on the pollution level sensed by the pollution level sensor.

* * * * *